US006455696B2

(12) United States Patent
Hayashi et al.

(10) Patent No.: US 6,455,696 B2
(45) Date of Patent: Sep. 24, 2002

(54) PROCESS FOR PREPARING 2,6-DICHLOROPURINE

(75) Inventors: Taketo Hayashi; Hiroharu Kumazawa; Junichi Nishikawa, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/895,317

(22) Filed: Jul. 2, 2001

(30) Foreign Application Priority Data

Jul. 10, 2000 (JP) ........................................ 2000-208450
Jun. 13, 2001 (JP) ........................................ 2001-179050

(51) Int. Cl.$^7$ ............................................. C07D 473/40
(52) U.S. Cl. ....................................................... 544/264
(58) Field of Search ........................................ 544/264

(56) References Cited

U.S. PATENT DOCUMENTS

| 2,844,576 A | 7/1958 | Goldman et al. |
| 3,314,938 A | 4/1967 | Kawashima et al. |

FOREIGN PATENT DOCUMENTS

| JP | 45-11508 | 4/1970 |

OTHER PUBLICATIONS

N. F. Myasoedov, et al., Radiokhimiya, vol. 23, No. 4, pps. 607–613, "Addition of a Tritium Label to Components of Nucleic Acids by Hydrogenolysis of the Corresponding Precursors", 1981 (with English translation).

S. E. Keeling, et al., Bioorganic & Medicinal Chemistry Letters, vol. 10, pps. 403–406, "The Discovery and Synthesis of Highly Potent, $A_{2a}$ Receptor Agonists", 2000.

S. B. Ha, et al., Bioorganic & Medicinal Chemistry Letters, vol. 7, No. 24, pps. 3085–3090, "New Base–Altered Adenosine Analogues: Synthesis and Affinity at Adenosine $A_1$ and $A_{2a}$ Receptors", 1997.

Harnden, J. Chem. Soc. Perkins 1, 2207 (1989).*

Dhanda, J. Chem. Soc. Perkins 1, 3469 (1999).*

Niiya, J. Med Chem 35, 4557 (1992).*

G. B. Elion et al., Studies on Condensed Pyrimidine Systems. XVII. Some Halogenopurines, *J. Am. Chem. Soc. 78*, 3508–10 (1956).

R. K. Robins, et al., Pyrimidines. IV. The Synthesis of Several New Chloro Substituted Pyrimidines, *J. Org. Chem.*, 19, 930–33 (1954).

J. A. Montgomery, et al., Synthesis of Potential Anticancer Agents. XI. $N^{2,6}$–Alkyl Derivatives of 2,6–Diaminopurine, *Cancer Research*, 15, 485 (1955).

* cited by examiner

*Primary Examiner*—Mark L Berch
(74) *Attorney, Agent, or Firm*—Oblon, Spivak, McClelland, Maier & Neustadt, P.C.

(57) ABSTRACT

A process for preparing 2,6-dichloropurine including chlorinating 2-amino-6-chloropurine with a chlorine source in the presence of a diazotizating agent.

16 Claims, No Drawings

PROCESS FOR PREPARING 2,6-DICHLOROPURINE

BACKGROUND OF THE INVENTION

1. Field of the Invention

The present invention relates to a process for preparing 2,6-dichloropurine. More specifically, the present invention relates to a process for preparing 2,6-dichloropurine, which can be suitably used as a raw material for nucleoside and nucleotide analogues which are useful as pharmaceuticals.

2. Discussion of the Related Art

As a process for preparing 2,6-dichloropurine, there have been known the following processes:

(A) a process comprising chlorinating xanthine with pyrophosphoryl chloride as disclosed in *J. Am. Chem. Soc.* 78, 3508–10 (1956);

(B) a process comprising chlorinating hypoxanthine or N-oxide of 6-chloropurine with phosphorus oxychloride as disclosed in Japanese Examined Patent Publication Sho 45-11508 and U.S. Pat. No. 3,314,938;

(C) a process comprising four steps using a barbituric acid derivative as a starting material as disclosed in *J. Org. Chem.* 19, 930(1954) and *J. Am. Chem. Soc.* 80, 404–8(1958);

(D) a process comprising cyclizing 2,4-dichloro-5,6-diaminopyrimidine as disclosed in U.S. Pat. No. 2,844,576; and the like.

However, there are some defects in process (A) in that the pyrophosphoryl chloride used as a chlorinating agent is complicated to prepare. In process A, pyrophosphoryl chloride is obtained from phosphorous oxychloride via a complicated procedure requiring a high reaction temperature of 165° C, a corrosion resistant reaction vessel and a 19-hour reaction time.

In addition, all of the processes (A) to (D) have long preparation steps and require complicated preparation procedures.

An object of the present invention is to provide a process capable of conveniently preparing 2,6-dichloropurine by using an inexpensive starting material.

These and other objects of the present invention will be apparent from the following description.

SUMMARY OF THE INVENTION

According to the present invention, there is provided a process for preparing 2,6-dichloropurine comprising the step of chlorinating 2-amino-6-chloropurine with a chlorine source in the presence of a diazotizing agent.

DETAILED DESCRIPTION OF THE INVENTION

One of the features of the present invention is that the process for preparing 2,6-dichloropurine comprises the step of chlorinating 2-amino-6-chloropurine with a chlorine source in the presence of a diazotizing agent.

2-amino-6-chloropurine is used as a starting material and is readily available, since 2-amino-6-chloropurine has been industrially widely prepared.

The diazotizing agent includes, for instance, alkali metal nitrites, such as sodium nitrite and potassium nitrite; alkyl esters of nitrous acid of which the alkyl moiety has 2 to 6 carbon atoms, such as t-butyl nitrite and isoamyl nitrite; nitrosyl chloride; nitrosylsulfuric acid; nitrogen monoxide; and the like. Among them, sodium nitrite is preferable because it is inexpensive and easily available. In addition, the alkyl esters of nitrous acid are preferable, because they increase the reactivity. The alkali metal nitrite can be dissolved in water before use since the alkali metal nitrite is solid at room temperature.

The amount of the diazotizating agent is 1 to 5 mol, preferably 1 to 2 mol per one mol of 2-amino-6-chloropurine, from the viewpoints of increasing reactivity and economics.

Representative examples of the chlorine source include metal chlorides, chlorinating agents, and the like. These chlorine sources can be used alone or in an admixture including at least two kinds of sources.

The metal chloride includes lithium chloride, potassium chloride, sodium chloride, calcium chloride, magnesium chloride, zinc chloride, nickel chloride, cuprous chloride, cupric chloride, and the like. Among them, lithium chloride is preferable from the viewpoints of increasing reactivity and improving yield.

The chlorinating agent includes chlorine, hydrochloric acid, thionyl chloride, alkyl chlorides such as methyl chloride, N-chlorosuccinimide, and the like. Among them, hydrochloric acid is preferable from the viewpoints of cost and improving yield. The concentration of hydrochloric acid is preferably not less than 10%.

It is preferable that the chlorine source is a combination of the metal chloride and the chlorinating agent, from the viewpoints of increasing reactivity and improving yield.

Among the combinations of the metal chloride and the chlorinating agent, it is preferable that the metal chloride is lithium chloride and the chlorinating agent is chlorine, N-chlorosuccimide or thionyl chloride, from the viewpoints of increasing reactivity, improving yield and suppressing the generation of by-products. It is more preferable that the metal chloride is lithium chloride and the chlorinating agent is chlorine.

When the metal chloride is used as the chlorine source, an acid can be added to the metal chloride. The acid includes acetic acid, propionic acid, formic acid, phosphoric acid and the like. Among them, acetic acid is preferable, from the viewpoints of increasing reactivity and suppressing the generation of by-products. As to the combination of the metal chloride and the acid, it is preferable that the metal chloride is lithium chloride and the acid is acetic acid, from the viewpoints of increasing reactivity, improving yield and suppressing the generation of by-products.

When the chlorine source is composed of the metal chloride alone or the chlorinating agent alone, it is desired that the amount of the chlorine source is 1 to 50 mol, preferably 5 to 20 mol per one mol of 2-amino-6-chloropurine, from the viewpoint of increasing reactivity, suppressing the generation of by-products and increasing economic advantages.

When the combination of the metal chloride and the chlorinating agent is used as the chlorine source, the ratio of the metal chloride to the chlorinating agent (molar ratio of the metal chloride/the chlorinating agent), is preferably 1/1 to 10/1, more preferably 2/1 to 6/1. In this case, it is desired that the amount of the chlorine source is 1 to 10 mol, preferably 3 to 6 mol per one mol of 2-amino-6-chloropurine.

In the present invention, first 2-amino-6-chloropurine can be suspended or dissolved in a solvent.

The solvent includes, for instance, water, organic solvents such as N,N-dimethylformamide and N,N- dimethylacetamide, and the like. The amount of the solvent is not limited to that which is specified, and can be altered by proper adjustment. In the case where hydrochloric acid or the combination of the metal chloride and the acid is used as the chlorine source, a solvent is not used, since the acid acts as a solvent. Therefore, when the acid is employed, 2-amino-6-chloropurine can be suspended in the acid.

Also, an alkali metal hydroxide, ammonia or the like can be added to the solvent in order to increase the solubility of 2-amino-6-chloropurine, and thereby 2-amino-6-chloropurine can be partly or completely dissolved.

2-Amino-6-chloropurine can be chlorinated by properly mixing the suspension or solution of 2-amino-6-chloropurine with the chlorine source and a diazotizating agent.

The reaction temperature during the chlorination depends upon the kinds of the chlorine source and the diazotizating agent. It is desired that the reaction temperature is −20° to 100° C., preferably −10° to 60° C., from the viewpoints of increasing reactivity and suppressing formation of the by-products.

The reaction time depends upon the reaction conditions and the like. The reaction time is usually from 1 to several hours.

The resulting reaction solution can be subjected to an after-treatment in an ordinary method to collect the resulting 2,6-dichloropurine.

The 2,6-dichloropurine can be collected by, for instance, a method comprising neutralizing the reaction solution with a base such as sodium hydroxide, potassium hydroxide, potassium carbonate or sodium carbonate or its aqueous solution to cause precipitation, and collecting precipitated crystals by filtration; or a method comprising extracting 2,6-dichloropurine with acetonitrile or ethyl acetate.

After the extraction, the formed 2,6-dichloropurine can be collected as crystals by concentrating the extract. Thereafter, 2,6-dichloropurine can be purified by an ordinary method.

Thus, a desired compound 2,6-dichloropurine can be conveniently prepared from an inexpensive compound as a starting material.

EXAMPLES

The present invention will be more specifically described on the basis of the following examples, without intending to limit the present invention thereto.

Example 1

To 209.4 g of a 35% aqueous hydrochloric acid (2.00 mol) was added 33.9 g (0.20 mol) of 2-amino-6-chloropurine. A solution prepared by dissolving 17.9 g (0.26 mol) of sodium nitrite in 30 mL of water was added to the above mixture in a thin stream. The mixture was stirred at 15° to 20° C. for 1 hour.

After the termination of the reaction, the resulting reaction solution was diluted with 300 mL of water, and 229 g of an about 40% aqueous sodium hydroxide was added in a thin stream to adjust its pH to 13.

Next, the reaction solution was extracted seven times with 400 mL of acetonitrile. The resulting extracts were combined, and the combined extracts were dried over anhydrous sodium sulfate. After drying, the residual solution was filtered, and the filtrate was concentrated under reduced pressure. 300 mL of water was added to the concentrated residue, and the mixture was neutralized with acetic acid to precipitate crystals. Thereafter, the mixture was heated to 75° to 80° C., and stirred for 1 hour. Next, the mixture was cooled to 0° to 10° C. and stirred for 1 hour. Subsequently, the precipitated crystals were collected by filtration, washed with 50 mL of water, and dried under reduced pressure, to give 12.2 g of white crystals of 2,6-dichloropurine (yield: 32.4%).

Melting point: 180° C. (literature value: 179° to 181.5° C.)

$^1$H-NMR (400 MHZ, DMSO-$d_6$): $\delta$(ppm)=8.74 (s, 1H), 14.15 (s, 1H)

Example 2

In 500 g of N,N-dimethylformamide was dissolved 100 g (2.36 mol) of lithium chloride. Thereafter, the mixture was cooled, 100 g (0.590 mol) of 2-amino-6-chloropurine was added thereto, and the mixture was stirred. To the resulting suspension was added 43.0 g (0.607 mol) of chlorine gas and 76.8 g (0.708 mol) of t-butyl nitrite at the same time at 10° to 40° C. over a period of 1 hour. After the termination of the addition, the chlorination reaction was carried out by stirring the mixture at 10° to 40° C. for 2 hours.

After the termination of the reaction, 500 g of water was added in a thin stream to the reaction solution, and the reaction solution was analyzed by high-performance liquid chromatography. As a result, it was found that 78.7 g of 2,6-dichloropurine was contained in the reaction solution. The reaction yield was 70.6%.

Next, the resulting reaction solution was extracted four times with 541 g of ethyl acetate. The extracts were combined, and thereafter washed with 200 g of water and 228 g of a 12% aqueous sodium thiosulfate. Subsequently, the washed extracts were re-extracted once with 150 g of 4N-aqueous sodium hydroxide and twice with 150 g of 2N-aqueous sodium hydroxide. The resulting alkali extracts were combined, and thereafter its pH was adjusted to 5 with a 35% hydrochloric acid to precipitate crystals. After the filtration, the resulting crystals were washed with 200 g of water, and thereafter dried at 60° C. under reduced pressure, to give 59.0 g of pale yellowish crystals of 2,6-dichloropurine (yield: 52.9%). The physical properties of the resulting 2,6-dichloropurine were the same as those in Example 1.

Example 3

The reaction was carried out in the same manner as in Example 2 except that 88.5 g (0.708 mol) of isoamyl nitrite was used in place of 76.8 g (0.708 mol) of tert-butyl nitrite.

The resulting reaction solution was analyzed. As a result, it was found that the reaction yield of 2,6-dichloropurine was 57.0%.

Example 4

The reaction was carried out in the same manner as in. Example 3 except that 500 g of N,N-dimethylacetamide was used in place of 500 g of N,N-dimethylformamide.

The resulting reaction solution was analyzed. As a result, it was found that the reaction yield of 2,6-dichloropurine was 65.8%.

Example 5

The reaction was carried out in the same manner as in Example 2 except that 88.5 g (0.708 mol) of isoamyl nitrite was used in place of 76.8 g (0.708 mol) of tert-butyl nitrite, and that 97.2 g (0.728 mol) of N-chlorosuccimide was used in place of 43.0 g (0.607 mol) of chlorine gas.

The resulting reaction solution was analyzed. As a result, it was found that the reaction yield of 2,6-dichloropurine was 63.8%.

Example 6

The reaction was carried out in the same manner as in Example 2 except that 75.8 g (0.637 mol) of thionyl chloride was used in place of 43.0 g (0.607 mol) of chlorine gas, and that 88.5 g (0.708 mol) of isoamyl nitrite was used in place of 76.8 g (0.708 mol) of tert-butyl nitrite.

The resulting reaction solution was analyzed. As a result, it was found that the reaction yield of 2,6-dichloropurine was 60.6%.

Example 7

To 40 mL of glacial acetic acid were added 5.1 g (30.0 mmol) of 2-amino-6-chloropurine and 6.4 g (150 mmol) of lithium chloride, and thereafter 3.11 g (45.0 mmol) of sodium nitrite was added thereto, and the reaction solution was stirred at 50° to 55° C. for 4 hours.

After the termination of the reaction, the resulting reaction solution was cooled to room temperature, and 100 mL of water was added in a thin stream to precipitate the crystals. The precipitated crystals were separated by filtration.

The resulting filtrate was neutralized with 122.5 g of a 20% aqueous sodium hydroxide, and thereafter the neutralized mixture was extracted twice with 300 mL of ethyl acetate. The extracts were combined and concentrated under reduced pressure.

To the concentrated residue was added 37 mL of water to re-crystallize the product. The precipitated crystals are collected by filtration, washed with 5 mL of water, and thereafter dried under reduced pressure, to give 1.5 g of white crystals of 2,6-dichloropurine (yield: 27.2%).

The resulting 2,6-dichloropurine crystals were identical in melting point and NMR to those of the product obtained in Example 1.

Example 8

To 75 mL of water were added 17.0 g (0.10 mol) of 2-amino-6-chloropurine, 4.4 g (0.11 mol) of sodium hydroxide, and 10.4 g (0.15 mol) of sodium nitrite.

The resulting solution was added in a thin stream to 104.2 g (1.00 mol) of a 35% hydrochloric acid at a temperature of 0° to 5° C. over one hour.

Thereafter, the mixture was stirred at the same temperature for one hour. After the termination of the reaction, the mixture was treated in the same manner as in Example 1, to give 6.6 g of white crystals of 2,6-dichloropurine (yield: 35.0%).

The resulting 2,6-dichloropurine crystals were identical in melting point and NMR to those of the product obtained in Example 1.

It can be seen from the above results that according to the process of Examples 1 to 8, a desired compound, 2,6-dichloropurine can be conveniently prepared from an inexpensive compound, 2-amino-6-chloropurine.

Numerous modifications and variations of the present invention are possible in light of the above teachings. It is therefore to be understood that within the scope of the appended claims, the invention may be practiced otherwise than as specifically described herein.

What is claimed is:

1. A process for preparing 2,6-dichloropurine, comprising chlorinating 2-amino-6-chloropurine with at least one chlorine source in the presence of a diazotizating agent, wherein the at least one chlorine source is selected from the group consisting of lithium chloride, potassium chloride, sodium chloride, calcium chloride, magnesium chloride, fly , zinc chloride, nickel chloride, hydrochloric acid, thionyl chloride, methyl chloride, and N-chlorosuccimide.

2. The process according to claim 1, wherein the diazotizating agent is chosen from the group consisting of alkali metal nitrites, alkyl esters of nitrous acid, nitrosyl chloride, nitrosylsulfuric acid and nitrogen monoxide.

3. The process according to claim 1, wherein the diazotizating agent is sodium nitrite.

4. The process according to claim 1, wherein the diazotizating agent is an alkyl ester of nitrous acid.

5. The process according to claim 1, wherein the diazotizating agent is present in an amount of 1 to 5 mol per one mol of 2-amino-6-chloropurine.

6. The process according to claim 1, wherein the diazotizating agent is present in an amount of 1 to 2 mol per one mol of 2-amino-6-chloropurine.

7. The process according to claim 1, wherein the chlorinating is performed in the further presence of chlorine gas.

8. The e process according to claim 1, further comprising suspending or dissolving the 2-amino-6-chloropurine in a solvent.

9. The process according to claim 8, further comprising adding an alkali metal hydroxide to the solvent.

10. The process according to claim 1, wherein the at least one chlorine source is lithium chloride.

11. The process according to claim 1, wherein the at least one chlorine source is hydrochloric acid.

12. The process according to claim 11, wherein the concentration of hydrochloric acid is not less than 10%.

13. The process according to claim 1, wherein the at least one chlorine source is selected from the group consisting of lithium chloride, N-chlorosuccimide and thionyl chloride.

14. The process according to claim 13, wherein the chlorinating is performed in the further presence of chlorine gas.

15. The process according to claim 1, wherein the reaction temperature is −20° C. to 100° C.

16. The process according to claim 1, wherein the reaction temperature is −10° C. to 60° C.

* * * * *